United States Patent
Ashdown (10) Patent No.: US 11,931,470 B2
(45) Date of Patent: Mar. 19, 2024

(54) VISIBLE LIGHT CHROMOPHORE EXCITATION FOR MICROORGANISM CONTROL

(71) Applicant: SUNTRACKER TECHNOLOGIES LTD., Victoria (CA)

(72) Inventor: Ian Edward Ashdown, West Vancouver (CA)

(*) Notice: Subject to any disclaimer, the term of this patent is extended or adjusted under 35 U.S.C. 154(b) by 0 days.

(21) Appl. No.: 18/548,866

(22) PCT Filed: Mar. 24, 2023

(86) PCT No.: PCT/CA2023/050399
§ 371 (c)(1),
(2) Date: Sep. 1, 2023

(87) PCT Pub. No.: WO2023/197060
PCT Pub. Date: Oct. 19, 2023

(65) Prior Publication Data
US 2024/0050603 A1    Feb. 15, 2024

Related U.S. Application Data

(60) Provisional application No. 63/329,732, filed on Apr. 11, 2022.

(51) Int. Cl.
*A61L 2/08* (2006.01)
(52) U.S. Cl.
CPC ...................... *A61L 2/084* (2013.01)
(58) Field of Classification Search
CPC ............. A61L 2/08; A61L 2/084; A61L 9/018
See application file for complete search history.

(56) References Cited

U.S. PATENT DOCUMENTS 11,122,747 B2    9/2021   Ashdown et al.
11,266,855 B2 *  3/2022   Enwemeka .......... A61N 5/0603
(Continued)

FOREIGN PATENT DOCUMENTS

WO    2007/012875         2/2007
WO    WO-2018152255 A1 *  8/2018    ............ A61M 21/00

OTHER PUBLICATIONS

Downes, L. R., and T. Blunt. 1877. "Research on the Effect of Light Upon Bacteria and Other Organisms," Proc. Royal Society of London 26:488-500.

(Continued)

*Primary Examiner* — Timothy C Cleveland
(74) *Attorney, Agent, or Firm* — Damien G Loveland; Valuetech Patent Agency Inc.

(57) ABSTRACT

Visible light disinfection is a healthcare technology wherein violet light is used to inactivate pathogens such as bacteria, fungi, and viruses. The present invention overcomes the limitations of continuous irradiance in whole-room environments by pulse width modulation of the light sources and increasing the instantaneous irradiance while maintaining average irradiance and hence light power requirements. The invention further discloses the use of multispectral light sources wherein the pulse modulation frequencies are synchronized and the phase of the spectral components are offset in order to maximize synergistic or antagonistic responses to intracellular chromophore excitation.

20 Claims, 3 Drawing Sheets

(56) References Cited

U.S. PATENT DOCUMENTS

| | | | |
|---|---|---|---|
| 2018/0117193 A1 | 5/2018 | Yadav et al. | |
| 2018/0193501 A1* | 7/2018 | Ufkes | A61L 2/10 |
| 2019/0125904 A1 | 5/2019 | Weeks, Jr. | |
| 2020/0360548 A1 | 11/2020 | Klubben, III et al. | |
| 2021/0277463 A1* | 9/2021 | Rothberg | H01S 3/10061 |

OTHER PUBLICATIONS

Grzybowski, A., and K. Pietrzak. 2012. "From Patient to Discoverer—Niels Ryberg Finsen (1860-1904)—the Founder of Phototherapy in Dermatology," Clinics in Dermatology 30:451-455.

Ward, H. M. 1894. "The Action of Light on Bacteria—III," Philosophical Trans. Royal Society of London B: Biology 185:961-986.

Møller, K. I., et al. 2005. "How Finsen's Light Cured Lupus vulgaris," Photodermatology, Photoimmunology & Photomedicine 21(3):118-124.

Tomb, R. M., et al. 2018. Review of the Comparative Susceptibility of Microbial Species to Photoinactivation Using 380-480 nm Violet-Blue Light, Photochemistry and Photobiology 94(3):445-458.

Maclean, M., et al. 2008. "High-Intensity Narrow-Spectrum Light Inactivation and Wavelength Sensitivity of Staphylococcus aureus," FEMS Microbiology Letters 285:227-232.

Halstead, F. D., et al. 2019. "Violet-Blue Light Arrays at 405 nm Exert Enhanced Antimicrobial Activity for Disinfection of Monomicrobial Nosocomial Biofilms," Applied and Environmental Microbiology 85(21): 1-16.

California Energy Commission 2019 Building Energy Efficiency Standards for Residential and Nonresidential Buildings, Table 140.6-C.

Bache, S. E., et al. 2017, "Universal Decontamination of Hospital Surfaces in an Occupied Inpatient Room with a Continuous 405 nm Light Source," J. Hospital Infection 98(1):P67-73.

Gillespie, J. B., et al. 2017. "Efficacy of Pulsed 405-nm Light-Emitting Diodes for Antimicrobial Photodynamic Inactivation: Effects of Intensity, Frequency, and Duty Cycle," Photomedicine and Laser Surgery 35(3):150-156.

Masson-Meyers, D., et al. 2019. "Pulsed 450 nm Blue Light Significantly Inactivates Propionibacterium acnes more than Continuous Wave Blue Light," J. Photochemistry and Photobiology B: Biology 202:111719.

Enwemeka, C. S. et al. 2021. "Pulsed Blue Light Inactivates Two Strains of Human Coronavirus," J. Photochemistry and Photobiology B: Biology 222:112282.

Hessling, M., et al. 2017. "Photoinactivation of Bacteria by Endogenous Photosensitizers and Exposure to Visible Light of Different Wavelengths—A Review on Existing Data," FEMS Microbiology Letters 364.

Gwynne, P. J., and M. P. Gallagher. 2018. "Light as a Broad-Spectrum Antimicrobial," Frontiers in Microbiology 9 Article 119.

Pathak, J., et al. 2018 "Mechanisms of Photoprotection in Cyanobacteria," in A. K. Mishra et al. (Eds.), Cyanobacteria: From Basic Science to Applications. Academic Press.

Lipovsky, A., et al. 2009. "Sensitivity of Staphylococcus aureus Strains to Broadband Visible Light," Photochemistry and Photobiology 85:255-260.

Rathnasinghe, R., et al. 2021. "The Virucidal Effects of 405 nm Visible Light on SARS-CoV-2 and Influenza A Virus," Scientific Reports 11(11):19470.

Rutala, W. A., et al. 2018. "Antimicrobial Activity of a Continuous Visible Light Disinfection System" Infectious Control Hospital Epidemiology 39(10):1250-1258.

Meng, Q., et al. 2019, "Blue Radiation Interacts with Green Radiation to Influence Growth and Predominantly Controls Quality Attributes of Lettuce," J. American Society of Horticultural Science 145(2):1-13.

Zhen, S. and B. Bugbee. 2019. "Far-red Photons Have Equivalent Efficiency to Traditional Photosynthetic Photons: Implications for Redefining Photosynthetically Active Radiation," Plant, Cell & Environment 2020:1-14.

V.V. Bumah et al. 2020. "Pulsed 450 nm blue light suppresses MRSA and Propionibacterium acnes in planktonic cultures and bacterial biofilms," Journal of Photochemistry and Photobiology. B, Biology (2020).

Irina Dokukina, et al. 2017 "New Perspectives on an Old Issue: A Comparative MS-CASPT2 and OM2-MRCI Study of Polyenes and Protonated Schiff Bases", Photochemistry and Photobiology, 2017, 93:1345-1355.

* cited by examiner

VISIBLE LIGHT CHROMOPHORE EXCITATION FOR MICROORGANISM CONTROL

TECHNICAL FIELD

The subject matter of the present invention relates to the use of optical radiation to influence microbial activity. In particular, the optical radiation is visible, with one or more monochromatic wavelengths.

BACKGROUND

Visible light disinfection is a healthcare technology wherein violet light is used to inactivate pathogens such as bacteria, fungi, and viruses. Unlike germicidal lamps emitting ultraviolet-C radiation, visible light does not pose the considerable risks of photokeratitis ("snow blindness") and erythema ("sunburn") for room occupants. With the availability of inexpensive and efficient violet LEDs (light-emitting diodes), the technology is being adopted by major luminaire manufacturers for everything from hospital operating theatres to residential kitchens.

Despite appearances, visible light disinfection is by no means a new technology. The ancient Egyptians reported the health benefits of sun exposure some six millennia ago, while ancient Greek, Roman and Arabic cultures similarly recognized the therapeutic values of sunlight. The benefits of phototherapy (or more specifically heliotherapy) were given scientific support by Downes, L. R., and T. Blunt. 1877. "Research on the Effect of Light Upon Bacteria and Other Organisms," Proc. Royal Society of London 26:488-500, who reported that bacteria were inactivated by sunlight, and that violet-blue light was the most effective.

The work of Downes and Blunt inspired Niels Finsen, a Danish medical researcher, to investigate further. After initial experiments in the early 1890s with natural light, he developed an apparatus using electric carbon arcs that would later become known as the "Finsen light" (Grzybowski, A., and K. Pietrzak. 2012. "From Patient to Discoverer—Niels Ryberg Finsen (1860-1904)—the Founder of Phototherapy in Dermatology," Clinics in Dermatology 30:451-455).

Finsen began his experiments using common glass lenses to focus the electric arc emission, but knew from the work of Ward, H. M. 1894. "The Action of Light on Bacteria—III," Philosophical Trans. Royal Society of London B: Biology 185:961-986, and others that ultraviolet radiation was germicidal, and so he replaced these lenses with fused quartz. However, as reported by Møller, K. I., et al. 2005. "How Finsen's Light Cured Lupus vulgaris," Photodermatology, Photoimmunology & Photomedicine 21(3):118-124, Finsen used methylthioninium chloride ("methylene blue") in solution as a heat-absorbing filter. Likely unknown to Finsen, this dye also absorbs ultraviolet radiation with wavelengths shorter than 340 nm. The Finsen light therefore produced ultraviolet-A radiation and visible light, but no germicidal ultraviolet-B radiation.

In WO 2007/012875, Anderson et al. disclosed a system and method for inactivating gram-positive bacteria such as methicillin-resistant *Staphylococcus aureus* (MRSA), coagulese-negative *Staphylococcus* (CONS), *Streptococcus*, *Enterococcus* and *Clostridium* species by means of exposure to visible light within the spectral range of 400 to 500 nm. It has since been determined (e.g., Tomb, R. M., et al. 2018. "Review of the Comparative Susceptibility of Microbial Species to Photoinactivation Using 380-480 nm Violet-Blue Light, Photochemistry and Photobiology 94(3):445-458) that many different species of gram-positive and gram-negative bacteria, fungi, yeasts, and some viruses can be inactivated by species-specific doses of visible light. The optimal wavelength has been determined to be 405±5 nm for maximum disinfection efficacy (Maclean, M., et al. 2008. "High-Intensity Narrow-Spectrum Light Inactivation and Wavelength Sensitivity of *Staphylococcus aureus*," FEMS Microbiology Letters 285:227-232). This system and method have recently been commercialized in the form of architectural luminaires that emit both blue light for disinfection and white light for general illumination, for example SpectraClean™ luminaires as manufactured by Hubbell Lighting Components (Elgin, IL). These luminaires are typically equipped with arrays of 405 nm lighting-emitting diodes to provide visible light disinfection radiation, and phosphor-coated "white light" LED arrays to provide general illumination.

A disadvantage of visible light disinfection for whole rooms such as hospital in-patient rooms and operating theaters, however, is that the irradiance levels on exposed surfaces are typically limited to 0.1 to 0.5 mW/cm 2 (e.g., Halstead, F. D., et al. 2019. "Violet-Blue Light Arrays at 405 nm Exert Enhanced Antimicrobial Activity for Disinfection of Monomicrobial Nosocomial Biofilms," Applied and Environmental Microbiology 85(21): 1-16) in order to comply with International Commission on Non-Ionizing Radiation Protection (ICNIRP) guidelines on exposure limits for incoherent visible radiation, and by building standards (e.g., California Energy Commission 2019 Building Energy Efficiency Standards for Residential and Nonresidential Buildings, Table 140.6-C) that mandate maximum allowable power per unit area for lighting (typically less than 10 W/m$^2$, or 1.0 mW/cm$^2$).

A limit of, for example, 0.5 mW/cm$^2$, means that the surface will receive a dose of 25 J/cm$^2$ of disinfecting blue light over a period of 14 hours, which is a typical daily operating time for hospital in-patient rooms. Such doses have been shown to inactivate on the order of 90 percent of some infectious bacterial pathogens commonly found in hospital settings (e.g., Bache, S. E., et al. 2017, "Universal Decontamination of Hospital Surfaces in an Occupied Inpatient Room with a Continuous 405 nm Light Source," J. Hospital Infection 98(1):P67-73), but there are many other infectious pathogens (including bacteria, yeasts, fungi, and viruses) that require considerably greater doses to achieve 90 percent inactivation, e.g., in TABLE 1—Common pathogen doses required for 90 percent reduction. (Source: Tomb et al. 2018).

TABLE 1

| Pathogen | Species | J/cm$^2$ Dose Min. | J/cm$^2$ Dose Max. |
|---|---|---|---|
| Bacteria | *Acinetobacter baumannii* | 2 | 26 |
| | *Bacillus cereus* | 27 | 665 |
| | *Campylobacter jejuni* | 0.3 | 3.4 |
| | *Clostridium difficile* | 13 | 736 |
| | *Clostridium perfingens* | 10 | |
| | *Corynebacterium striatum* | 4 | 64 |
| | *Enterococcus faecalis* | 64 | 410 |
| | *Escherichia coli* | 5 | 612 |
| | *Klebsiella pneumoniae* | 16 | 263 |
| | *Listeria monocytogenes* | 17 | 1121 |
| | *Mycobacterium terrae* | 57 | |
| | *Proteus vulgaris* | 31 | |
| | *Pseudomonas aeruginosa* | 4 | 1020 |
| | *Salmonella enteritidis* | 72 | 544 |
| | *Serratia marcescens* | 128 | 337 |

TABLE 1-continued

| Pathogen | Species | J/cm² Dose Min. | J/cm² Dose Max. |
|---|---|---|---|
| | Shigella sonnei | 36 | 608 |
| | Staphylococcus aureus | 9 | 1200 |
| | Staphylococcus epidermidis | 9 | |
| Fungi | Aspergillus niger | 181 | 23000 |
| | Candida albicans | 2 | 327 |
| | Saccharomyces cerevisiae | 58 | 66 |

Gillespie, J. B., et al. 2017. "Efficacy of Pulsed 405-nm Light-Emitting Diodes for Antimicrobial Photodynamic Inactivation: Effects of Intensity, Frequency, and Duty Cycle," Photomedicine and Laser Surgery 35(3):150-156, reported that when exposing MRSA bacteria to 116 mW/cm 2 of 405 nm radiation, varying the pulse width duty cycle from 25 to 100 percent had little effect on the dose required to achieve the same degree of inactivation. The pulse width modulation (PWM) frequency was varied from 100 Hz to 10 kHz, with 1000 Hz showing the best performance, and with 35 percent energy savings for a 50 percent duty factor. The authors speculated that the cell porphyrins become saturated with continuous exposure, and that the off period of each cycle enables the absorbed light to generate ROS (reactive oxygen species) with fewer photons being absorbed unnecessarily.

Masson-Meyers, D., et al. 2019. "Pulsed 450 nm Blue Light Significantly Inactivates Propionibacterium acnes more than Continuous Wave Blue Light," J. Photochemistry and Photobiology B: Biology 202:111719, reported that a duty cycle of 33 percent and a PWM frequency of 33 kHz was optimal for 450 nm radiation treating acne vulgaris caused by the Propionibacterium acnes bacterium. The experiments involved microLEDs mounted on flexible plastic sheets that were applied to the infected skin, but remarkably the required irradiance to achieve 100 percent eradication of the bacteria was 40 to 100 times less than previously reported results for in vitro experiments involving MRSA bacteria. However, this involved repeated treatments every four hours that were timed to coincide with the replication cycle of P. acnes, as opposed to single exposures of bacterial cultures in the laboratory.

Bumah et al. (2020) demonstrated that pulsed 450 nm blue light suppresses the formation of MRSA and Propionibacterium acnes bacteria in planktonic cultures and bacterial biofilms. Irradiances of 3 mW/cm 2 and three doses of 7.6 J/cm 2 were sufficient to completely eradicate MRSA bacteria in solution, while 2 mW/cm 2 and 5 J/cm 2 were sufficient to eradicate P. acnes bacteria. Assuming that "eradication" means 99.9 percent inactivation, this implies that the doses required for 90 percent inactivation would be 1.9 J/cm 2 and 1.3 J/cm 2 respectively.

A common assumption is that visible light disinfection is the result of intracellular (endogenous) porphyrins absorbing and being excited by 405 nm photons, and then generating ROS such as singlet oxygen and hydrogen peroxide, which being cytotoxic inactivate the cells. However, Enwemeka, C. S. et al. 2021. "Pulsed Blue Light Inactivates Two Strains of Human Coronavirus," J. Photochemistry and Photobiology B: Biology 222:112282, reported that pulsed blue light inactivates enveloped coronaviruses, so there are presumably other intracellular mechanisms involved, and which do not necessarily require 405 nm irradiation.

Figure 1:
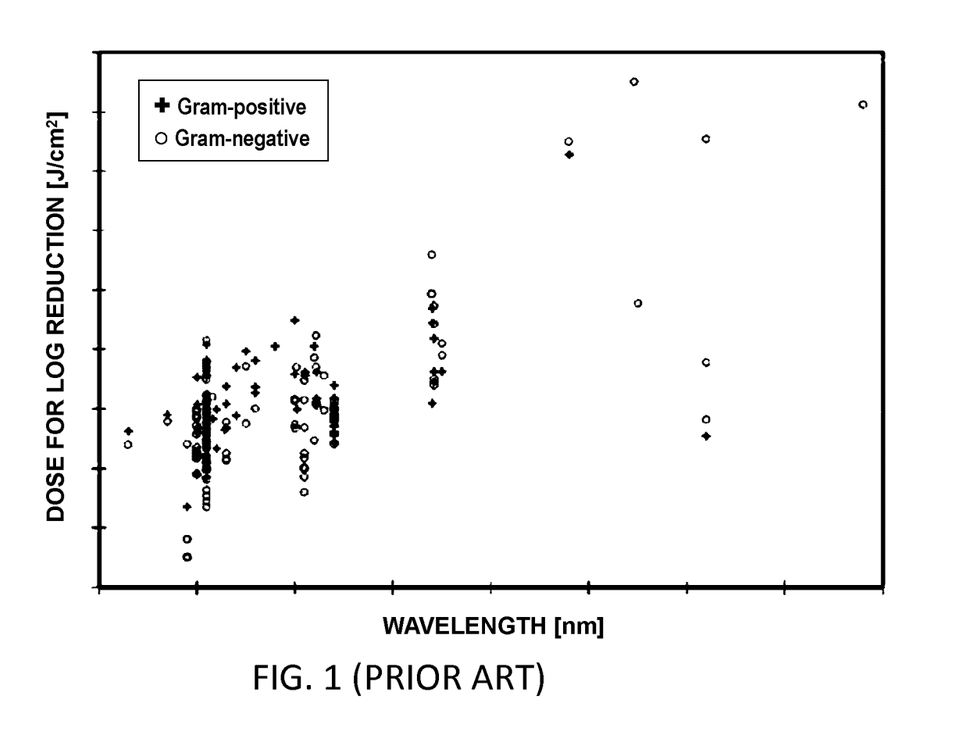
FIG. 1 shows prior art bacterial susceptibility versus wavelength.

Most visible light disinfection studies conducted to date have focused on the spectral region of 385 nm to 420 nm. However, bactericidal effects of visible light have been demonstrated with wavelengths of up to 740 nm, as shown in FIG. 1 (from Hessling, M., et al. 2017. "Photoinactivation of Bacteria by Endogenous hotosensitizers and Exposure to Visible Light of Different Wavelengths—A Review on Existing Data," FEMS Microbiology Letters 364). These are presumably due to the absorption haracteristics of different endogenous photosensitizers that absorb photons and enerate cytotoxic ROS that inactivate the bacterial or fungal cells. However, the dose required for inactivation generally increases exponentially with wavelength.

As noted by Gwynne, P. J., and M. P. Gallagher. 2018. "Light as a Broad-Spectrum Antimicrobial," Frontiers in Microbiology 9 Article 119, however, much of the visible light spectrum has yet to be explored. There are known endogenous photosensitizers with absorptance peaks at 405 nm (porphyrins) and 450 nm (riboflavin), but there are other potential endogenous chromophores that may result in anomalous susceptibility for particular pathogen species or broad classes.

There is a similar situation with plant biology research, wherein many different photopigments, including chlorophylls, phytochromes, cryptochromes, carotenes, xanthophylls, anthocyanins, phototropins and more are being explored to elucidate their photobiological functions. More recently, it has been realized that there are complex interactions between these photopigments, and that the spectral power distribution of the photobiologically active radiation from 280 nm to 800 nm incident on the plants can be manipulated to achieve desirable results, such as producing compact plants, advancing or delaying the onset of flowering, and the production of secondary metabolites for food and medicinal purposes.

As reported by Gillespie et al. (2017) and Masson-Meyers et al. (2019), pulsed blue light appears to be more efficacious than continuous blue light, with the duty cycle appearing to have little effect on the required dose. From the perspective of excited chromophores generating ROS or initiating other photochemical and non-photochemical reactions, this implies chromophore saturation.

Pathak, J., et al. 2018 "Mechanisms of Photoprotection in Cyanobacteria," in A. K. Mishra et al. (Eds.), Cyanobacteria: From Basic Science to Applications. Academic Press, reports that while cyanobacteria rely on photosynthetically active radiation (PAR) in order to perform photosynthesis, the photosynthetic process may become saturated at high light levels. (The PAR spectrum of 400 nm to 700 nm roughly corresponds to that of the visible light spectrum.)

It is chlorophyll A and B in photosynthetic organisms that absorb blue and red light respectively, assisted by various other accessory photopigments such as beta-carotene. Each such photopigment acts a chromophore, but what they have in common is that the organisms have evolved mechanisms to protect themselves from excess energy when the photosynthetic process becomes saturated, including nonphotochemical processes, fluorescence, and photochemistry. These processes are triggered by the generation of ROS, which initially serve as signaling molecules, but whose overproduction can lead to oxidative stress and cell inactivation.

The cited literature has established that visible light induces the overproduction of ROS in cells, leading to oxidative stress and, in sufficient doses, cellular damage and cell inactivation. As indicated by Hessling et al. (2017) in FIG. 1, the studies have examined the effects of quasimonochromatic LEDs from 360 nm to 740 nm. In addition, a few studies have examined the susceptibility of bacteria to broadband visible light. For example, Lipovsky, A., et al. 2009. "Sensitivity of *Staphylococcus aureus* Strains to Broadband Visible Light," Photochemistry and Photobiology 85:255-260 employed a halogen lamp with a filter having a spectral bandwidth of approximately 400 nm to 800 nm, while Rathnasinghe, R., et al. 2021. "The Virucidal Effects of 405 nm Visible Light on SARS-CoV-2 and Influenza A Virus," Scientific Reports 11(11):19470 considered fluorescent and phosphor-coated light-emitting diode arrays emitting "white" light with varying correlated color temperatures (CCTs). Rutala, W. A., et al. 2018. "Antimicrobial Activity of a Continuous Visible Light Disinfection System" Infectious Control Hospital Epidemiology 39(10): 1250-1258, further investigated visible light disinfection luminaires with both blue and "white" light-emitting diode arrays.

Examples of interactions in plant biology include Meng, Q., et al. 2019, "Blue Radiation Interacts with Green Radiation to Influence Growth and Predominantly Controls Quality Attributes of Lettuce," J. American Society of Horticultural Science 145(2):1-13, and Zhen, S. and B. Bugbee. 2019. "Far-red Photons Have Equivalent Efficiency to Traditional Photosynthetic Photons: Implications for Redefining Photosynthetically Active Radiation," Plant, Cell & Environment 2020:1-14, where far-red photons synergistically interact with shorter-wavelength photons to increase leaf photochemical efficiency. However, this relates to plant biology and not microbiology.

For whole-room disinfection, building standards mandate maximum irradiances, based on maximum allowable power per unit area. However, these limitations are based on average power with continuous irradiation. If the visible light for disinfection purposes is pulsed through pulsed modulation or similar techniques, the instantaneous irradiance during the on cycle is inversely proportional to the pulsed modulation duty factor. For example, with a duty factor of ten percent, the maximum allowable irradiance is ten times that of continuous irradiance.

This background is not intended, nor should be construed, to constitute prior art against the present invention.

SUMMARY

The inventor has recognized a need for a system and method of visible light disinfection that avoids the need for unachievably high irradiances and doses to achieve 90 percent inactivation or more of common pathogens. The activity of the pathogens, or more broadly microorganisms, may be inhibited or promoted with the application of visible light. The microorganisms are illuminated with two different wavelengths of pulsed, visible light. During the pulses of light, two or more chromophores in the microorganism are excited, which leads to the activity of the microorganism being either inhibited or promoted, depending on the microorganism and the chromophores. The pulses of the different wavelengths are at a frequency that is a whole number multiple of a fundamental frequency. There may be a phase difference between the two different pulse trains.

Disclosed is a method for exciting two different chromophores in a microorganism, the method comprising illuminating the microorganism with first light having a first pulse frequency and a first wavelength between 380 nm and 750 nm, while illuminating the microorganism with second light having a second pulse frequency and a second wavelength between 380 nm and 750 nm, wherein the second wavelength is different to the first wavelength, wherein the first and second pulse frequencies are integral multiples of a fundamental frequency, and wherein a cycle of the first light has a zero, positive or negative phase difference with respect to a corresponding cycle of the second light.

Also disclosed is a luminaire comprising: a first light emitting element (LEE) that emits first light at a first pulse frequency with a first wavelength between 380 nm and 750 nm; and a second LEE that emits second light at a second pulse frequency with a second wavelength between 380 nm and 750 nm; wherein the second wavelength is different to the first wavelength; wherein the first and second pulse frequencies are integral multiples of a fundamental frequency; and wherein a cycle of the first light has a controllable phase difference with respect to a corresponding cycle of the second light.

Further disclosed is a system for exciting two different chromophores in a microorganism, the system comprising: a luminaire having a first light emitting element (LEE) that emits first light at a first pulse frequency with a first wavelength between 380 nm and 750 nm, and a second LEE that emits second light at a second pulse frequency with a second wavelength between 380 nm and 750 nm, wherein the second wavelength is different to the first wavelength, wherein the first and second pulse frequencies are integral multiples of a fundamental frequency, and wherein a cycle of the first light has a controllable phase difference with respect to a corresponding cycle of the second light; a driver coupled to drive each LEE with an independently variable duty factor and an independently variable peak radiant flux output and to control the phase difference; a sensor configured to detect a parameter of an environment of the microorganism; and a controller configured to adjust, based on the parameter, either or both of a peak radiant flux and a duty factor, in either or both of the first light and the second light, in order to maintain a predetermined rate of chromophore excitation in other microorganisms that are the same as said microorganism.

This summary provides a simplified, non-exhaustive introduction to some aspects of the invention, without delineating the scope of the invention.

DETAILED DESCRIPTION

A. Definitions

A "chromophore" is a chemical group capable of spectrally selective absorption of optical radiation resulting in coloration of certain organic compounds. The absorption is often incidental to any biological function of the chemical group.

A "driver" means an electrical device that regulates the pulsed modulation to LEEs.

The term "general illumination" means lighting that is typically used in a home, office or factory, which is comfortable for the occupants in relation to the tasks they are performing.

The term light-emitting element ("LEE") is used to define any device that emits radiation in any region or combination of regions of the electromagnetic spectrum for example, the visible region, infrared and/or ultraviolet region, when activated by applying a potential difference across it or passing a current through it, for example. Therefore, an LEE can have monochromatic, quasi-monochromatic, polychromatic or broadband spectral emission characteristics. Examples of LEEs include semiconductor, organic, or polymer/polymeric light-emitting diodes, optically pumped phosphor coated light-emitting diodes, optically pumped nano-crystal light-emitting diodes or other similar devices as would be readily understood by a worker skilled in the art. Each LEE generates optical radiation with one or more monochromatic wavelengths in the range of 200 nm to 3000 nm. Specifically, each LEE may generate optical radiation in the visible spectrum with one or more wavelengths from about 380 nm to about 750 nm. An LEE may have multiple constituent LEEs of the same or different types.

The term "microorganism" or "microbe" refers to bacteria, fungi, yeasts, viruses, bacteriophages and protozoans. Microorganisms may be beneficial or pathogenic.

The term "monochromatic light" herein refers to light with a very narrow bandwidth, such as typically emitted by a laser or laser diode.

The term "quasimonochromatic light" herein refers to light with a narrow bandwidth, such as light that is typically emitted by an LED.

The term "white light" is used herein in the layman's sense, to refer to light that appears to be white or close to white, rather than in the scientific sense in which it refers to the continuum of the visible spectrum.

Individual parts of the system may be referred to as modules. The term "module" can refer to any component in this invention and to any or all of the features of the invention without limitation. A module may be a software, firmware or hardware module, and may be or be located in a luminaire, driver, controller or other computing device.

The term "processor" is used to refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). The processor performs the steps in the flowchart, whether they are explicitly described as being executed by the processor or whether the execution thereby is implicit due to the steps being described as performed by code or a module. The processor, if comprised of multiple processors, may be located together or geographically separate from each other. The term includes virtual processors and machine instances as in cloud computing or local virtualization, which are ultimately grounded in physical processors.

The terms "pulse modulation" and "pulse modulated" mean any technique utilizing a digitally modulated pulse to switch LEEs on and off at a desired frequency, and includes pulse width modulation (PWM), pulse code modulation (PCM), randomized PCM, pulse position modulation (PPM), pulse-amplitude modulation (PAM), pulse-duration modulation (PDM), and any other similar techniques or pulse modes as would be readily understood by a worker skilled in the art. One or more different pulse modulation techniques may be used concurrently or alternately on one or more serial or parallel channels. As would be readily understood by a worker skilled in the art the "on" periods relative to the "off" periods represent the pulse modulation duty factor.

Reactive oxygen species ("ROS") are highly reactive chemicals formed from dioxygen molecules ($O_2$) by means of one-electron excitation to produce either singlet oxygen ($^1O_2$) or one-electron reduction to produce a superoxide radical ($O_2^-$), which may be a precursor to a peroxide radical ($HO_2^-$), a peroxide ion ($O_2^{2-}$) hydrogen peroxide ($H_2O_2$), or a hydroxyl radical (OH). In a biological context, ROS are byproducts of the normal metabolism of oxygen, and have roles in cell signaling and homeostasis. They are normally eliminated by antioxidative intracellular mechanisms, but they otherwise can cause irreversible damage if they oxidize cellular components such as proteins, lipids (cell membrane), and DNA, thereby preventing from performing their functions, in a process called oxidative stress.

B. Principle

None of the prior art studies considered the possibility of synergetic or antagonistic interactions between different wavelength bands in microorganisms. The existence of interactions between chromophores in bacterial and yeast cells, and possibly in the shells of enveloped viruses, which upon excitation by multiple wavelengths of visible light, as well as ultraviolet-A (UV-A) and near-infrared (NIR) radiation, may stress pathogens and so prevent them from multiplying.

When an endogenous chromophore such as a porphyrin or a flavin in a bacterial cell absorbs a photon, one of its electrons is promoted into a higher-energy orbital, elevating the chromophore from its ground state into a short-lived, electronically excited state. It may then decay from this excited state to the ground state, typically within a nanosecond to a microsecond.

All pathogens exposed to light have evolved under the spectral distribution of natural daylight, and so it is possible that cellular processes involved in managing oxidative stress may rely on different chromophores. Whether or not these chromophores harvest energy from incident photons to perform their respective functions, exciting them with photons whose wavelengths are within the chromophores' spectral absorption peaks may disrupt their activity and so increase oxidative stress within the cells.

There are synergetic or antagonistic interactions between chromophores involved in the processes responsible for removing ROS under oxidative stress conditions. It is not necessary that these chromophores, including proteins and lipids, be involved in photochemical reactions, but rather that they may be electronically excited by incident photons in a manner that disrupts their normal activity. This activity may not necessarily involve the removal of the ROS if the disruption results in environmental stress leading to cell inactivation. If these interactions are influenced by the application of multispectral but not necessarily broadband radiation, it is possible to employ a multispectral LEE with wavelengths tuned to the absorption peaks of two or more of the corresponding chromophores such that its antimicrobial efficacy is greater than that of a quasimonochromatic or broadband LEE. In other words, a radiant flux that is sufficient to have an effect, when it is incident upon a microorganism from a combination of two monochromatic LEEs, is less than the radiant flux that would be required to achieve the same effect using quasimonochromatic or broader band light that encompasses the two wavelengths of the monochromatic LEEs.

By synchronizing the frequencies and phases of two or more spectral components of a multispectral LEE, further benefits may be obtained compared to a pulsed, single spectral component. Such benefits may include a further increase in efficacy of pathogen reduction, for example. As one example, an LEE with a blue component with a spectral range of 400 nm to 410 nm and a green component with a spectral range of 520 nm to 530 nm may be modulated with a frequency of 1000 Hz and a duty factor of 20 percent, but where the phase of the green component is offset by 90 degrees (i.e., 250 microseconds delay) from that of the blue component.

C. Exemplary System

Figure 2:
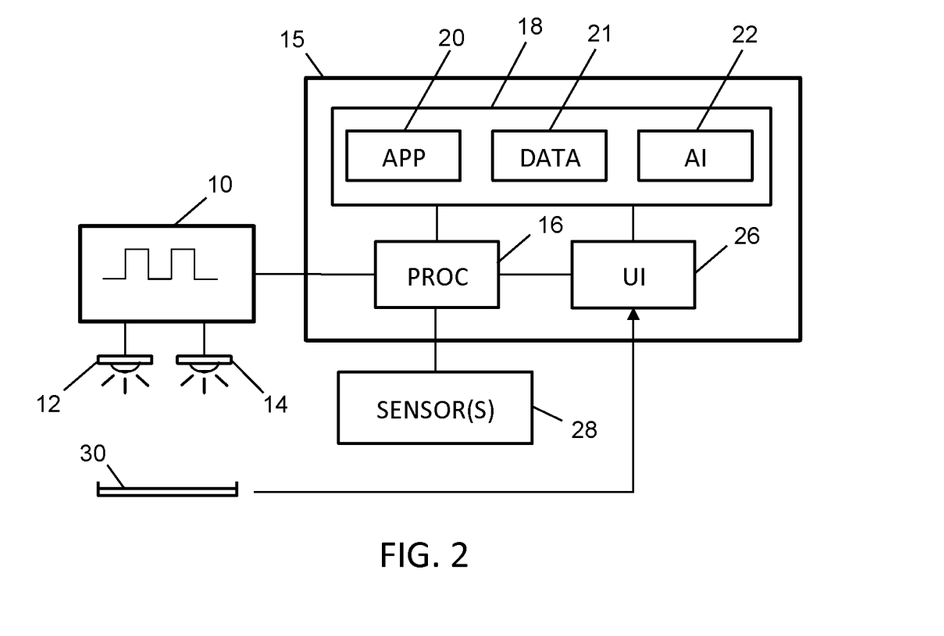
FIG. 2 is a block diagram of a system, according to an embodiment of the present invention.

Referring to FIG. 2, an exemplary system is shown. A driver 10 is connected to LEEs 12, 14, and may drive them identically or differently. A controller 15 connected to the driver includes a processor 16 connected to a computer readable memory 18, which stores computer readable instructions in the form of an application 20. This application controls the driver 10, e.g. by specifying the output parameters of the LEEs, such as the frequency of the pulse modulation, the peak intensity, the duty factor, the phase between two or more LEE driving signals, etc. Also stored in the memory are data 21 and an AI (artificial intelligence) application 22. A user interface 26 is also connected to the processor and one or more sensors 28 are connected to the processor. Cultures 30 of pathogens grown on agar may be measured before and after being subjected to the illumination from the LEEs and the data fed back into the system via the user interface, for example. The processor 16 executes the instructions in the application 20 to provide one or more functions of the system.

Figure 3:
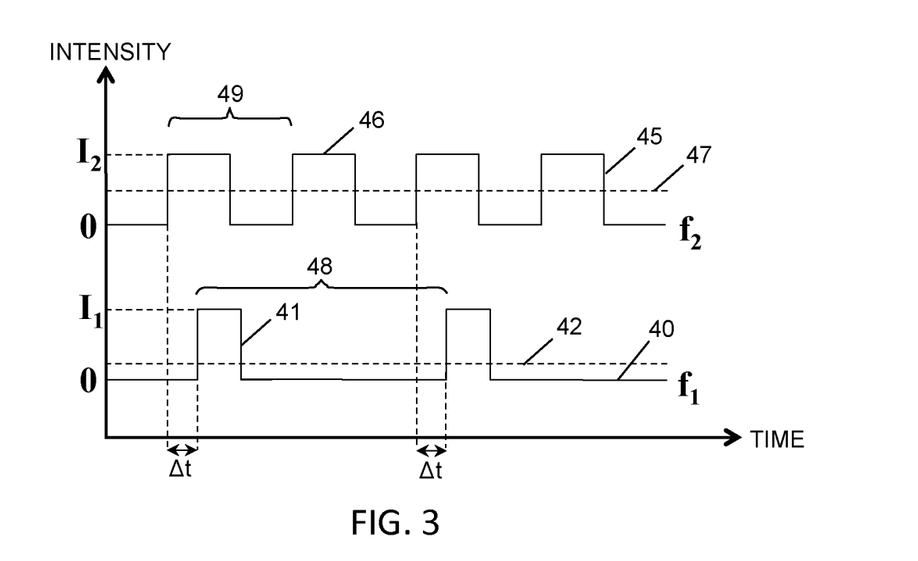
FIG. 3 shows two PWM intensity profiles according to an embodiment of the present invention.

Referring to FIG. 3, the intensity outputs of two LEEs are shown. The lower graph shows the output 40 of one LEE 12 with pulses 41 at a pulse frequency of $f_1$ and peak radiant flux $I_1$. The average intensity is shown by the dashed line 42. The upper graph shows the output 45 of another LEE 14 with pulses 46 at a pulse frequency of $f_2$ and peak radiant flux 12. The average intensity is shown by dashed line 47. A time difference $\Delta t$ is present between the start of pulses 41 and the start of corresponding pulses selected from pulses 46. The time difference $\Delta t$ is a positive, zero or negative value and is measured between the start of a cycle 48 of the output from LEE 12 and the start of a corresponding cycle 49 of the output from LEE 14. Some or all of the parameters $\Delta t$, $I_1$, $I_2$, $f_1$, $f_2$, pulse modes and duty factors may be adjusted by the controller 15, subject to any constraints on the system, such as $f_1$ and $f_2$ being integral multiples of a common or fundamental frequency.

D. Exemplary Embodiments

In a first embodiment, a pulse modulated LEE has a radiant flux output with variable duty factor and variable radiant flux output, such that the radiant flux output can be increased with decreasing duty factor to provide constant average radiant flux. The LEE may have a wavelength of 405 nm, for example, or a wavelength in the range 400-410 nm, or in the range 200-3000 nm for embodiments in which non-visible light is used. Referring to FIG. 2, such an LEE may be represented by LEE 12 or LEE 14. In variations of this embodiment, multiple identical LEEs 12, 14 may be combined and driven in synchronization with each other to provide the pulsed light output.

In a second embodiment, a multispectral pulse modulated LEE has a radiant flux output with variable duty factor and variable radiant flux output, wherein the radiant flux is comprised of two or more constituent LEEs with different spectral ranges. The constituent LEEs may have two different wavelengths in the range 400-700 nm, or in the range 200-3000 nm, for example, as there are embodiments in which both visible and non-visible wavelengths are used. Referring to FIG. 2, such a composite LEE may be represented by the combination of LEE 12 and LEE 14, for example where each of LEE 12 and LEE 14 have a different wavelength.

In a third embodiment, a multispectral pulsed modulated LEE has a radiant flux output with variable duty factor and variable radiant flux output, wherein the frequencies of the spectral component modulations are multiples of a fundamental frequency. The radiant flux is provided by two or more constituent LEEs with different spectral ranges, or with different monochromatic wavelengths. The constituent LEEs may have two different wavelengths in the range 400-700 nm, or in the range 200-3000 nm, for example. Referring to FIG. 2, such a composite LEE may be represented by the combination of LEE 12 and LEE 14, for example. Referring to FIG. 3, one of the constituent LEEs may have a first frequency $f_1$ of pulse modulation and a second one of the constituent LEEs may have a frequency $f_2$ of pulse modulation, where $f_2=2f_1$. In other variations of this embodiment, $f_2=3f_1$, or $f_2=4f_1$, for example, with other multiples also possible. In yet other variations of this embodiment, $f_1=nf_0$ and $f_2=mf_0$, where $f_0$ is the fundamental frequency and n and m are different integers, e.g. 2 and 3. That is, the ratio between the pulse frequencies is non-integral.

As discussed above, different chromophores have peak susceptibilities in different wavelength ranges (e.g., 400 to 410 nm and 520 to 530 nm) and at different pulse frequencies. It is reasonable to assume that different chromophores have different relaxation constants. Ideally, the pulse rate for each wavelength would be determined by this constant. However, having different pulse frequencies could lead to undesirable beat frequencies that could be visually noticeable. Assuming that the dependence on pulse frequency is reasonably low, such that a range of pulse frequencies does not significantly affect the susceptibility, then different chromophores may matched to different pulse frequencies that are multiples of a fundamental frequency. By applying light to one or both chromophores at a frequency that is not at, but relatively close to, the frequency of peak susceptibility allows for a simplification of the LEE driver by avoiding beat frequencies, while maintaining a significant and effective amount of susceptibility. A luminaire may therefore have one or more LEEs emitting in the range 400-410 nm and one or more other LEEs emitting in the range 520-530 nm, where the different LEEs have different pulse frequencies.

In a fourth embodiment, a multispectral pulsed modulated LEE has a radiant flux output with variable duty factor and variable radiant flux output, wherein the frequencies of the spectral component modulations are multiples of a fundamental frequency, and where the phases of the spectral components are offset from each other by predetermined amounts. The radiant flux is provided by two or more constituent LEEs with different spectral wavelengths. The constituent LEEs may have two different wavelengths in the range 400-700 nm, or in the range 200-3000 nm, for example. Referring to FIG. 2, such a composite LEE may be represented by the combination of LEE 12 and LEE 14, for example. Referring to FIG. 3, one of the constituent LEEs may have a pulsed intensity output 40 and a second one of the constituent LEEs may have a pulsed intensity output 45. The start of the pulses 41 of the output 40 are shown to lag the start of corresponding pulses 46 of the output 45 by a time $\Delta t$ relative to the start of every second pulse 46. The time $\Delta t$ represents a phase lag of output 40 compared to output 45. In other variations of this embodiment, the pulses 41 start in advance of the corresponding pulses 46, representing a phase lead of output 40 compared to output 45. In other variations of this embodiment, $f_1 = f_2$. In yet other variations of this embodiment, the pulses 41 and 46 do not overlap, or pulses 41 start at the same time as the respective ones of pulses 46 end.

In a fifth embodiment, a multispectral pulsed modulated LEE has a radiant flux output with variable duty factor and variable radiant flux output, wherein the frequencies of the spectral component modulations are multiples of a fundamental frequency, where the phases of the spectral components are offset from each other by predetermined amounts, and wherein the amplitudes of the spectral component modulations differ with respect to each other by predetermined amounts. Referring to FIG. 2, such a composite LEE may be represented by the combination of LEE 12 and LEE 14, for example. Referring to FIG. 3, one of the constituent LEEs may have a pulsed intensity output 40 with a peak radiant flux output $I_1$ and a second one of the constituent LEEs may have a pulsed radiant flux output 45 with a peak of $I_2$, where $I_1$ and $I_2$ are different. In a variation of this embodiment, one or both of the peak radiant fluxes may be independently adjusted, or they may both be adjustable while maintaining a constant ratio between the two.

In a sixth embodiment, the duty factors and radiant flux outputs of a pulse modulated LEE or multispectral pulsed modulated LEE may vary in response to external conditions, including time, ambient illumination, relative humidity, ambient temperature, air movement, salinity, and other environmental factors which may affect the growth or inhibition of pathogens. For example, in terms of determining a consistent exposure time, it may be advantageous to modulate the radiant flux in response to different or changing external conditions. These external conditions may be determined as a result of electronic monitors or may be entered manually through a user interface. In addition, feedback systems may be employed to automate the duty factors and radiant flux outputs of a pulse modulated LEE or multispectral pulse modulated LEE in response to external conditions. For example, a method may involve detecting, with a sensor, a parameter of an environment of the microorganism; and in response, adjusting either or both of a peak radiant flux and a duty factor, in either or both of the first light and the second light, in order to maintain a predetermined rate of chromophore excitation in other microorganisms that are the same as said microorganism.

Common means of determining pathogen inactivation are colony counts on agar plates. With sufficient time and patience, the relationship between different external conditions and inactivation rates may be explored and enumerated.

Referring to FIG. 2, one or more sensors 28 form part of or are connected to the system. The sensors may monitor a duration of a particular environment, ambient illumination, relative humidity, ambient temperature, air movement, salinity or any other factor which may influence the multiplication rate of pathogens. For example, if the environmental factors are known to promote a slower reproduction of a pathogen, then the peak intensity, duty cycle or frequency of the LEE output may be reduced to save energy while still maintaining a satisfactory pathogen reduction rate. Conversely if the environmental factors are known to promote a more rapid reproduction of a pathogen, then the peak intensity, duty cycle or frequency of the LEE output may be increased to maintain a satisfactory pathogen reduction rate.

In an additional embodiment, machine learning may be used to help determine the effect of specific conditions which affect a particular pathogen, including external conditions. This machine learning also helps to assess pathogen mutations, and determine changing conditions that affect the pathogen over time. Referring to FIG. 2, an AI application 22 is included in the system. The AI application takes as input the environmental conditions as indicated by the sensors 28, the intensity profiles of the LEEs, and the level or change in level of pathogens in the environment as determined from time to time by pathogen colony growth 30. Results from the colony growth may be input manually into the system via a user interface 26, or photographs (including at the microscope level) of the culture growth may be taken manually or automatically and input into the AI application.

E. Exemplary Applications

In a first application and referring to FIG. 2, pulsed LEEs 12, or 12 and 14, are incorporated in a dedicated architectural, industrial, or medical light source to provide visible light disinfection radiation.

Figure 4:
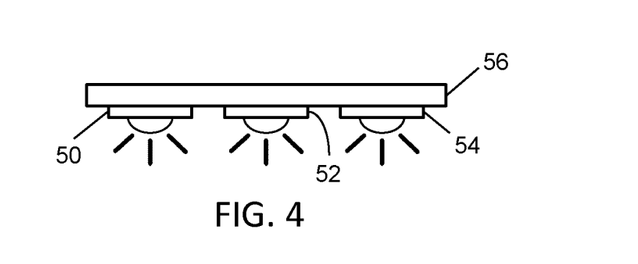
FIG. 4 is a schematic diagram of a luminaire, according to an embodiment of the present invention.

In a second application and referring to FIG. 4, pulsed LEEs 50, 54 with different monochromatic or quasimonochromatic wavelengths are incorporated in an architectural or industrial luminaire 56 with a "white light" LEE 52. For example, LEE 52 has a broad spectral output, or multiple broad spectral ranges, or multiple monochromatic or quasi-monochromatic wavelengths that appear to the human eye as white. The luminaire 56, as well as providing pathogen-reducing light, also provides general "white light" illumination from LEE 52 with a fixed or variable CCT and color rendering properties. Wavelengths of LEEs 50, 54 may be tuned to the absorption peaks of different chromophores in a microorganism. For example, LEE 50 may be a 405 nm LED tuned to a porphyrin and LEE 54 may be a 450 nm LED tuned to riboflavin.

In a third application, pulsed multispectral LEEs are incorporated in an architectural or industrial luminaire that also provides general "white light" illumination with a fixed or variable correlated color temperature, wherein the spectral power distribution (SPD) of the white light illuminant (LEE 52) is such that the combination of its SPD and that of the pulsed multispectral LEEs 50, 54 generates white light with a predetermined CCT and color rendering properties. For example, compared to a white light luminaire that would traditionally be used only for illumination of an interior space, one or more portions of the spectrum of the white light are removed and provided instead as pathogen-reducing light. As such, the majority of the white light for illumination may be provided at a higher frequency (e.g. 2 to 500 times higher than the fundamental frequency) than the pathogen-reducing light, while the luminaire 56 still appears to the human eye to output the same spectrum as the traditional luminaire. For example, the PWM frequency of commercial LED drives is between 20 kHz and 50 kHz, which minimizes the size of the smoothing capacitors. The PWM frequencies explored so far for disinfection purposes have been 100 Hz to 10 kHz.

In a fourth application, the pulsed multispectral LEEs are realized as pulse modulation-LEEs in a horticultural luminaire, e.g. luminaire 56 in FIG. 4. In a variation of this embodiment, LEE light emanates from optical components that are mounted on a substrate, each optical component being coupled to an optical fiber that delivers optical radiation combined from LEEs 12, 14 (FIG. 2) or 50, 52, 54, for example. A linear or elliptical holographic diffuser is located to diffuse the light emanating from the optical components. An example of this set-up of optical components may be seen in U.S. Pat. No. 11,122,747. The LEE wavelengths excite plant photopigments for predetermined physiological responses, and the light source intensities may be temporally modulated to maximize photosynthesis and control photomorphogenesis responses. The light may also kill the pathogens on the plants as well. However, the dependence of the photosynthetic process on visible light may complicate matters. This is where pulsed LEEs with small duty factors may be useful, in that the pulses of light do not significantly contribute to the Daily Light Integral for the plants, but they may be sufficient to inactive pathogens on the plant leaves, such as powdery mildew. Each LEE may be independently controlled. Optical fiber textiles may be used to provide the light output.

Figure 5:
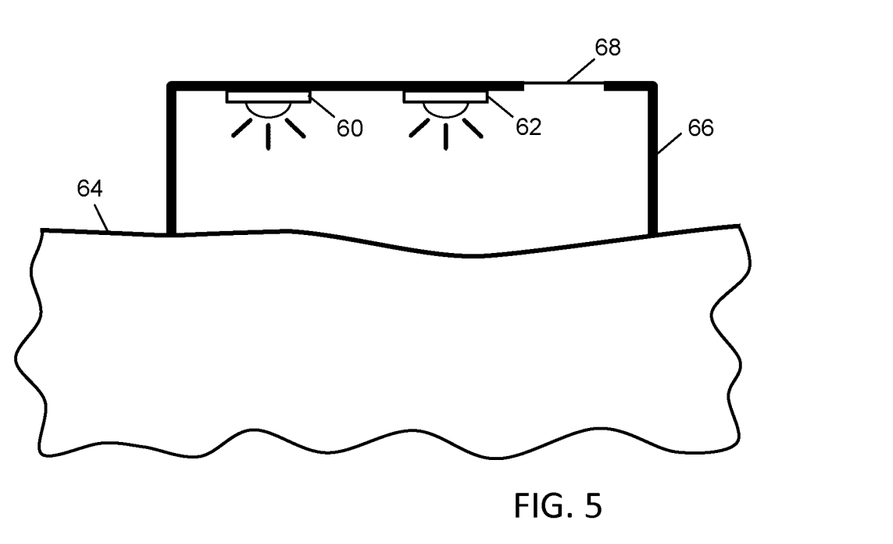
FIG. 5 is a schematic diagram of a light-treatment chamber, according to an embodiment of the present invention.

In a fifth application and referring to FIG. 5, the pulse modulated LEEs 60, 62 are incorporated in a medical light treatment system. The light treatment system comprises one or more LEEs for illuminating a part (e.g. skin) of a human or animal body 64 for light treatment. The light treatment system further comprises a housing 66 for emitting light towards the part of the human or animal body, and for at least partially covering the illuminated part of the human or animal body from view. The housing further comprises a window 68 for emitting light from an inner part of the housing away from the housing. An effect of the light treatment system according to the invention is that the window in the housing may be used as an indicator whether the light treatment system is operating and/or functioning well. Furthermore, the presence of a luminescent material, for example, on the window, may be used as an indicator for, for example, ultraviolet light, as part of the ultraviolet light may be converted by the luminescent material into visible light. Optical fiber textiles may be used to provide the light output and placed near on the part of the human or animal body.

Figure 6:
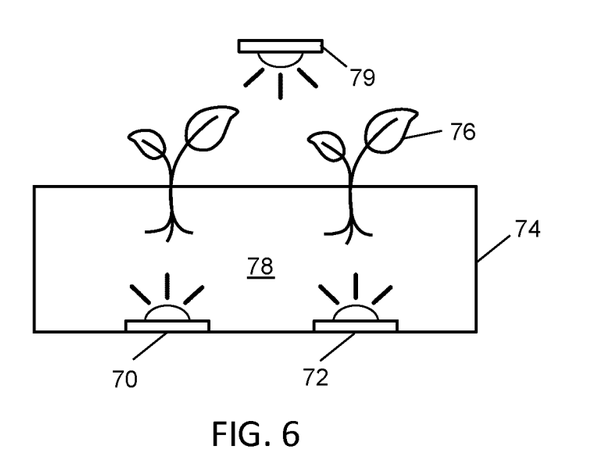
FIG. 6 is a schematic diagram of a plant-illumination apparatus, according to an embodiment of the present invention.

In a sixth application and referring to FIG. 6, the pulse modulated LEEs 70, 72 are incorporated in a biological lighting system 74 for controlling root growth of plants 76, wherein the optical radiation either prevents or promotes bacterial activity in the soil or other growth medium 78. Such a growth medium may be transparent or translucent. In some cases the growth medium may be soil, through which there is at least some penetration of the illumination. Bacterial activity that may be promoted by the applied light includes, for example, nutrient recycling, decomposition of organic matter, inhibition of diseases and reproduction. In another application, the LEE 79 may be used to illuminate the shoot system of the plants, to inhibit pathogens that may be present on it.

In addition to the pathogen-influencing illumination, the biological lighting system also provides further, temporally and spatially modulated photon flux output and spectral power distributions to plants on a circadian and circannual basis, or circadian and life cycle basis, to maximize effective and efficient growth in a horticultural setting. This additional irradiation, e.g. by LEE 79, may be applied to the shoot system, the roots, or both. The photon flux or irradiance output and the spectral power distribution are modulated to match circadian and circannual rhythms, with individual or multiple luminaires controlled through one or more controllers. Different lighting spectra can be employed depending on the direction of illumination. The photon flux or irradiance output and the spectral power distribution may be set as best suited for any particular plant species, and the system is also useful for raising animals.

Figure 7:
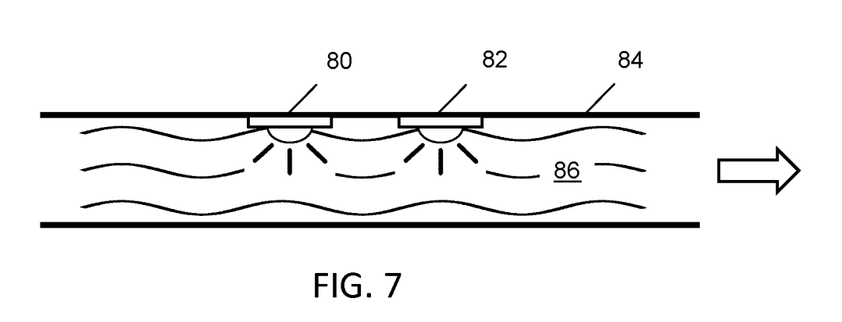
FIG. 7 is a schematic diagram of a water-disinfecting device, according to an embodiment of the present invention.

In a seventh application in FIG. 7, the pulsed LEEs 80, 82 are incorporated in a water purification system 84. As the water 86 flows through a pipe, for example, it is illuminated with the light from the LEEs 80, 82. The light reduces the number of pathogens in the water. In a variation of this embodiment, the water may be static, e.g. in a tank, while it is being illuminated.

F. Exemplary Method

Figure 8:
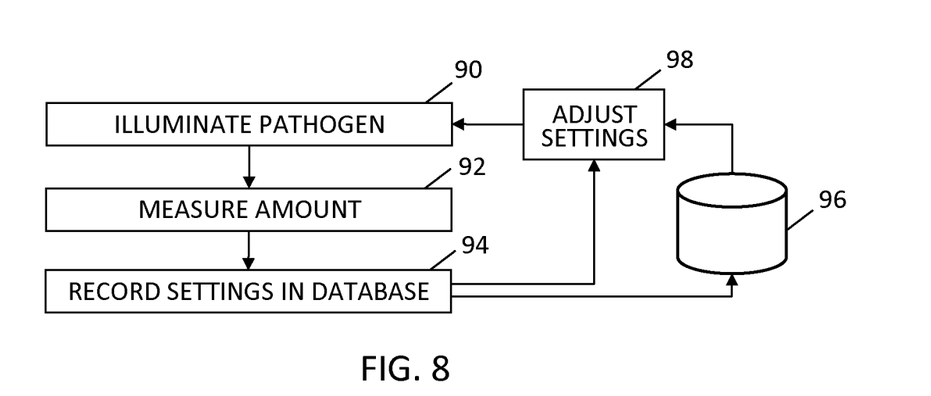
FIG. 8 is a flowchart of a method for inhibiting pathogens, according to an embodiment of the present invention.

Referring to FIG. 8, a method is shown by which data is fed back to the system in order to better control the luminaire. In step 90, an environment in which a pathogen is present or may be present is illuminated with the luminaire. The illumination may be, for example, illumination with two different monochromatic wavelengths of light, with pulse frequencies that are integral multiples of a fundamental frequency, and which may have a zero, positive or negative phase difference between the two. In step 92, the amount of pathogen in the environment is measured, which may involve, for example, taking a sample and growing a culture on an agar plate. In step 94, the results of the culture growth are recorded in a database 96, in relation to the parameters of light that was used for the illumination of the environment prior to taking the sample. In step 98, the settings of the parameters of the luminaire are changed, e.g. by changing the duty factor, the peak intensity, the frequency, the phase between two different wavelengths etc. The environment with the pathogen or possible presence of the pathogen is again illuminated in step 90, with the adjusted parameters, and the process cycles through multiple times. Over time, enough data is obtained for a person or an AI machine to determine optimum settings for the luminaire. In other cases, analytic or algorithmic relationships between the parameters of the luminaire and the inhibition of growth of the pathogen may be determined.

G. Variations

The present invention is herein described more fully with reference to the accompanying drawings, in which embodiments and applications of the invention are shown. This invention may, however, be embodied and applied in many different forms, and should not be construed as limited to the embodiments and applications described herein. Rather, these embodiments and applications are provided so that this disclosure will be thorough and complete, and will fully convey the scope of the invention to those skilled in the art.

Modules may be divided into constituent modules or combined into larger modules.

The system may be configured so that its output may be changed depending on the type of pathogen that is present in the space that is to be disinfected.

The system may be used for research purposes for the further investigation of how multiple pulsed wavelengths of illumination inhibit or promote the activity of different microorganisms.

Throughout the description, specific details have been set forth in order to provide a more thorough understanding of embodiments of the invention. However, the invention may be practised without these specific details. In other instances, well known elements have not been shown or described in detail and repetitions of steps and features have been omitted to avoid unnecessarily obscuring the invention. Embodiments, depending on their configuration, may exhibit all or fewer than all of the advantages described herein. Other advantages not mentioned may be present in one or more of the embodiments. Features from any of the embodiments may be combined with features from any of the other embodiments to form another embodiment within the scope of the invention. In general, unless otherwise indicated, singular elements may be in the plural and vice versa with no loss of generality. All quantities, parameters, wavelengths are examples only and others may be used in other embodiments. All ranges given include all subranges within the range. For example, if a range is given as m-q, then the ranges m-n, n-p and p-q are included, where n and p are any values that satisfy m<n<p<q.

Accordingly, the scope of the invention is to be construed in accordance with the substance defined by the claims.

I claim:

1. A method for exciting two different chromophores in a microorganism, the method comprising:
    illuminating the microorganism with first light having a first pulse frequency and a first wavelength between 380 nm and 750 nm; while
    illuminating the microorganism with second light having a second pulse frequency and a second wavelength between 380 nm and 750 nm;
    wherein the second wavelength is different to the first wavelength;
    wherein the first and second pulse frequencies are different;
    wherein the first and second pulse frequencies are integral multiples of a fundamental frequency; and
    wherein a pulse train of the first light has a zero, positive or negative phase difference with respect to a corresponding pulse train of the second light.

2. The method of claim 1, wherein the microorganism is in air, in water, in a horticultural growth medium, on mammalian skin, on a plant root or on a plant shoot system.

3. The method of claim 1, comprising providing further illumination, which, in combination with the first light and the second light, provides white light for general illumination with a predetermined correlated color temperature and predetermined color rendering properties.

4. The method of claim 3, wherein the further illumination has a pulse frequency of 2-500 times greater than the fundamental frequency.

5. The method of claim 1, comprising providing further illumination, which, in combination with the first light and the second light, provides light corresponding to a circadian cycle, circannual cycle or life cycle of a plant.

6. The method of claim 1, wherein each of the first and second wavelengths is tuned to an absorption peak of the corresponding chromophore.

7. The method of claim 1, wherein:
    the first light and the second light are monochromatic; and
    a radiant flux that is incident upon the microorganism from the first light and the second light combined is less than a radiant flux that would be required to achieve said excitation of the chromophores using quasimonochromatic or broadband light that encompasses the first and second wavelengths.

8. The method of claim 1, wherein the phase difference is non-zero.

9. The method of claim 1, further comprising:
    detecting, with a sensor, a parameter of an environment of the microorganism; and
    in response, adjusting either or both of a peak radiant flux and a duty factor, of either or both of the first light and the second light.

10. The method of claim 1, wherein each chromophore is a flavin or a porphyrin.

11. A luminaire comprising:
    a first light emitting element (LEE) that emits first light at a first pulse frequency with a first wavelength between 380 nm and 750 nm; and
    a second LEE that emits second light at a second pulse frequency with a second wavelength between 380 nm and 750 nm;
    wherein the second wavelength is different to the first wavelength;
    wherein the first and second pulse frequencies are different;
    wherein the first and second pulse frequencies are integral multiples of a fundamental frequency; and
    wherein a pulse train of the first light has a controllable phase difference with respect to a corresponding pulse train of the second light.

12. The luminaire of claim 11, wherein the first light and the second light are monochromatic.

13. The luminaire of claim 12, wherein the first wavelength is between 400-410 nm and the second wavelength is between 520-530 nm.

14. The luminaire of claim 11 further comprising one or more further LEEs that generate optical radiation with one or more wavelengths in a range of 200 nm to 3000 nm, wherein the optical radiation is monochromatic, polychromatic, multispectral or quasimonochromatic.

15. The luminaire of claim 14, wherein the optical radiation corresponds to a circadian cycle, a circannual cycle or a life cycle of a plant.

16. The luminaire of claim 11 further comprising one or more further LEEs that generate optical radiation with one or more wavelengths in a range of 380 nm to 750 nm.

17. The luminaire of claim 16, wherein the optical radiation is emitted at a pulse frequency 2-500 times greater than the fundamental frequency.

18. The luminaire of claim 11, wherein a ratio between the first and second pulse frequencies is non-integral.

19. A system for exciting two different chromophores in a microorganism, the system comprising:
    a luminaire having:
        a first light emitting element (LEE) that emits first light at a first pulse frequency with a first wavelength between 380 nm and 750 nm; and
        a second LEE that emits second light at a second pulse frequency with a second wavelength between 380 nm and 750 nm;
        wherein the second wavelength is different to the first wavelength;
        wherein the first and second pulse frequencies are different;
        wherein the first and second pulse frequencies are integral multiples of a fundamental frequency; and wherein a pulse train of the first light has a controllable phase difference with respect to a corresponding pulse train of the second light;

a driver coupled to drive each LEE with an independently variable duty factor and an independently variable peak radiant flux output and to control the phase difference;

a sensor configured to detect a parameter of an environment of the microorganism; and a controller configured to adjust, based on the parameter, either or both of a peak radiant flux and a duty factor, in either or both of the first light and the second light.

20. The method of claim 1, comprising controlling the phase difference.

* * * * *